(12) United States Patent
Ovadia et al.

(10) Patent No.: US 11,912,790 B2
(45) Date of Patent: Feb. 27, 2024

(54) PEPTIDE COMPOUNDS AND THERAPEUTIC USES OF SAME

(71) Applicant: Immunity Pharma Ltd., Mevasseret Zion (IL)

(72) Inventors: Eran Ovadia, Mevasseret Zion (IL); Avi Ben-Shimon, Ayanot (IL)

(73) Assignee: Immunity Pharma Ltd., Mevasseret Zion (IL)

( * ) Notice: Subject to any disclaimer, the term of this patent is extended or adjusted under 35 U.S.C. 154(b) by 0 days.

(21) Appl. No.: 17/254,867

(22) PCT Filed: Jul. 10, 2019

(86) PCT No.: PCT/IL2019/050774
§ 371 (c)(1),
(2) Date: Dec. 22, 2020

(87) PCT Pub. No.: WO2020/012478
PCT Pub. Date: Jan. 16, 2020

(65) Prior Publication Data
US 2021/0261615 A1    Aug. 26, 2021

(30) Foreign Application Priority Data

Jul. 11, 2018 (IL) .......................................... 260555

(51) Int. Cl.
*C07K 7/06* (2006.01)
*A61K 38/00* (2006.01)

(52) U.S. Cl.
CPC ................ *C07K 7/06* (2013.01); *A61K 38/00* (2013.01)

(58) Field of Classification Search
None
See application file for complete search history.

(56) References Cited

U.S. PATENT DOCUMENTS

| 7,087,711 | B2 * | 8/2006 | Ptashne .................. C12N 15/63 530/300 |
| 10,011,829 | B2 | 7/2018 | Fan |
| 2004/0204340 | A1 | 10/2004 | Hamilton et al. |
| 2007/0197444 | A1 | 8/2007 | Herman et al. |
| 2008/0267983 | A1 | 10/2008 | Herkel et al. |
| 2014/0088017 | A1 | 3/2014 | Ovadia et al. |
| 2016/0038571 | A1 | 2/2016 | Peti et al. |
| 2016/0090612 | A1 * | 3/2016 | Hattendorf ................ C12P 7/62 435/254.2 |
| 2023/0049549 | A1 | 2/2023 | Ovadia et al. |

FOREIGN PATENT DOCUMENTS

| CN | 101035554 | 9/2007 |
| EA | 202190249 | 5/2021 |
| JP | 2008-510796 | 4/2008 |
| WO | WO 2006/021954 | 3/2006 |
| WO | WO 2012/160563 | 11/2012 |
| WO | WO 2016/172722 | 10/2016 |
| WO | WO 2017/011338 | 1/2017 |
| WO | WO 2020/012478 | 1/2020 |
| WO | WO 2021/144798 | 7/2021 |

OTHER PUBLICATIONS

Blast results for PPLPY (retrieved from https://blast.ncbi.nlm.nih.gov/Blast.cgi on Feb. 16, 2022, 31 pages) (Year: 2022).*
Blast results for LPPLAYP (retrieved from https://blast.ncbi.nlm.nih.gov/Blast.cgi on Sep. 7, 2022, 41 pages) (Year: 2022).*
International Preliminary Report on Patentability dated Jan. 21, 2021 From the International Bureau of WIPO Re. Application No. PCT/IL2019/050774. (12 Pages).
International Search Report and the Written Opinion dated Jan. 22, 2020 From the International Searching Authority Re. Application No. PCT/IL2019/050774. (23 Pages).
Invitation to Pay Additional Fees, Communication Relating to the Results of the Partial International Search and the Provisional Opinion dated Oct. 4, 2019 From the International Searching Authority Re. Application No. PCT/IL2019/050774. (10 Pages).
Office Action and Search Report dated Nov. 19, 2018 From the Israel Patent Office Re. Application No. 260555. (10 Pages).
Dimri et al. "Specific Inhibition of Glucocorticoid-Induced Thymocyte Apoptosis by Substance P", The Journal of Immunology, XP055625708, 164(5): 2479-2486, Mar. 1, 2000.
Huang et al. "Electronic Interactions of I, I + 1 Dithioamides: Increased Fluorescence Quenching and Evidence for N-to-Pi Interactions", Chemical Communications, XP055656869, 52(50): 7798-7801, Jun. 14, 2016.
Mirgorodskaya et al. "Bradykinin Degradation Pathways in Human Blood Plasma", The FEBS Letters, XP025983822, 307(3): 263-266, Aug. 3, 1992.
Nomizu et al. "Convulsant Peptides Related to Corticotropin-Releasing Factor (CRF)", Brain Research, XP024276988, 505(2): 326-328, Dec. 29, 1989.
Strop et al. "Characterization of P15 Protease of Myeloblastosis Associated Virus by Specificity and Inhibition Studies", Database CAPLUS [Online], Database Accession No. 1990:94408 CAPLUS, 1989, Proceedings of the Colloquium C 52, 14th International Congress of Biochemistry, Prague, Czech Republic, Jul. 10-15, 1988, p. 141-153, Jul. 10, 1988.
Yoshida et al. "Bax-Inhibiting Peptide Derived From Mouse and Rat Ku70", Biochemical and Biophysical Research Communications, BBRC, XP028808286, 321(4): 961-966, Sep. 3, 2004.
Invitation to Pay Additional Fees, Communication Relating to the Results of the Partial International Search and the Provisional Opinion dated Apr. 14, 2021 From the International Searching Authority Re. Application No. PCT/IL2021/050044. (17 Pages).

(Continued)

*Primary Examiner* — Ronald T Niebauer

(57) ABSTRACT

Isolated peptides capable of reducing the amount of dexamethasone-induced spleen and/or thymus weight loss in a mouse are disclosed as well as uses thereof.

2 Claims, 2 Drawing Sheets

Specification includes a Sequence Listing.

(56) References Cited

OTHER PUBLICATIONS

Harris "PDK1 and PKB/AKT: Ideal Targets for Development of New Strategies to Structure-Based Drug Design", IUBMB Life, XP009041386, 55(3): 117-126, Mar. 2003.
Herkel et al. "Activation of the Akt-CREB Signalling Axis by A Proline-Rich Heptapeptide Confers Resistance to Stress-Induced Cell Desth and Inflammation", Immunology, XP055623927, 151(4): 474-480, Published Online May 16, 2017.
Opposition Report Dated Feb. 26, 2021 From the Superintendente De Industria Y Comercio de Columbia, Re Application No. NC2021/0001290. (9 Pages) Spanish.
International Search Report and the Written Opinion dated Jun. 7, 2021 From the International Searching Authority Re. Application No. PCT/IL2021/0500044. (20 Pages).
International Preliminary Report on Patentability dated Jul. 28, 2022 From the International Bureau of WIPO Re. Application No. PCT/IL2021/0500044. (13 Pages).
International Preliminary Report on Patentability dated Jul. 28, 2022 From the International Bureau of WIPO Re. Application No. PCT/IL2021/050044. (13 Pages).
English Summary Dated Apr. 13, 2023 of Notification About Necessity to Submit Additional Materials dated Mar. 28, 2023 From The Eurasian Patent Organization, The Eurasian Patent Office Re. 202190249. (2 Pages).
Notification About Necessity to Submit Additional Materials dated Mar. 28, 2023 From The Eurasian Patent Organization, The Eurasian Patent Office Re. 202190249 (3 Pages).
Notification of Office Action and Search Report dated Apr. 23, 2023 From the State Intellectual Property Office of the People's Republic of China Re. Application No. 201980041027.6 (10 pages).
Communication Pursuant to Article 94(3) EPC dated Oct. 10, 2022 From the European Patent Office Re. Application No. 19752749.2. (5 Pages).
Search Report and Written Opinion dated Sep. 20, 2022 From the Intellectual Property Office of Singapore, IPOS Re. Application No. 11202012773Q. (12 Pages).
Examination and Search Report dated Jun. 2, 2023 From the Republica de Colombia, Superintendencia de Industria y Comercio Re. Application No. NC2021/001290 and Its Summary Into English. (18 Pages).
Office Action dated Aug. 22, 2023 From the Israel Patent Office Re. Application No. 272074. (5 Pages).
Notice of Reason(s) for Rejection dated May 30, 2023 xFrom the Japan Patent Office Re. Application No. 2020-573032 and Its Translation Into English. (11 Pages).
Request for Examination and Search Report dated May 16, 2023 From the (ROSPATENT), Federal Government Institution of Industrial Property of the Federal Service of Intellectual Property, Patents and Trademark of the Russian Federation Re. Application No. 2021103167 and Its Summary in English. (9 Pages).
Translation Dated May 11, 2023 of Notification of Office Action and Search Report dated Apr. 23, 2023 From the State Intellectual Property Office of the People's Republic of China Re. Application No. 201980041027.6. (2 pages).
Notification About Necessity to Submit Additional Materials dated Dec. 13, 2022 From The Eurasian Patent Organization, The Eurasian Patent Office Re. 202292119 and Its Summary in English. (8 Pages).
Request for Substantive Examination and Search Report dated Dec. 20, 2022 From the Federal Government Institution, Federal Institute of Industrial Property of the Federal Service of Intellectual Property, Patents and Trademarks of the Russian Federation, FIPS Re. 2021103167 and its Summary in English. (13 Pages).

\* cited by examiner

PEPTIDE COMPOUNDS AND THERAPEUTIC USES OF SAME

RELATED APPLICATIONS

This application is a National Phase of PCT Patent Application No. PCT/IL2019/050774 having International filing date of Jul. 10, 2019, which claims the benefit of priority of Israel Patent Application No. 260555 filed on Jul. 11, 2018. The contents of the above applications are all incorporated by reference as if fully set forth herein in their entirety.

SEQUENCE LISTING STATEMENT

The ASCII file, entitled 84963Sequence—Listing.txt, created on Dec. 22, 2020, comprising 6,360 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to compositions and methods of using same for treating inflammatory and autoimmune diseases.

There is an unmet need for novel compositions that may serve to attenuate cellular and immune stress-response in normal tissue, in a manner that is specific, safe and effective, thereby reducing the severity of stress associated degenerative diseases and stress-induced inflammation.

The peptide LPPLPYP (SEQ ID NO: 2, also known as Stressin-1 and IPL344) is a short 7 amino acids peptide that protects cells of various types from pro-apoptotic pressures and activates the Akt signaling system. The structure of IPL344 resembles the binding sites of adaptor proteins. It has been proposed to have a mechanism of action which comprises mimicking such proteins and activating cell protective processes via Akt and possibly other pathways.

International Patent Application Publication Nos: WO 2006/021954 and WO2012/160563 disclose the use of LPPLPYP (SEQ ID NO: 2) peptide for treating diseases such as ALS.

SUMMARY OF THE INVENTION

According to an aspect of the present invention there is provided an isolated peptide being no longer than ten amino acids which comprises an amino acid sequence represented by the formula $X_1$-$X_2$-$X_3$-$X_4$-$X_5$-$X_6$ (SEQ ID NO: 17),
(i) wherein $X_1$ is proline, or an analogue or derivative thereof;
(ii) wherein $X_2$ is proline, or an analogue or thereof;
(iii) wherein $X_3$ is selected from the group of alanine, valine, leucine, cysteine, isoleucine, methionine and a derivative or analogue thereof;
(iv) wherein $X_4$ is selected from the group consisting of alanine, valine, serine and a derivative or analogue thereof;
(v) wherein $X_5$ is any amino acid;
(vi) wherein $X_6$ proline or an analogue or derivative thereof; and
(vii) wherein the peptide is capable of reducing the amount of dexamethasone-induced spleen and/or thymus weight loss in a mouse.

According to an aspect of the present invention there is provided an isolated peptide being no longer than six amino acids which comprises an amino acid sequence represented by the formula $X_1$-$X_2$-$X_3$-$X_4$-$X_5$ (SEQ ID NO: 1),
(i) wherein $X_1$ is proline or an analogue or derivative thereof;
(ii) wherein $X_2$ is proline or an analogue or derivative thereof;
(iii) wherein $X_3$ is selected from the group of alanine, valine, leucine, cysteine, isoleucine, methionine and a derivative or analogue thereof;
(iv) wherein $X_4$ is selected from the group consisting of alanine, valine, serine, proline and a derivative or analogue thereof;
(v) wherein $X_5$ is any amino acid; and
(vi) wherein the peptide is capable of reducing the amount of dexamethasone-induced spleen and/or thymus weight loss in a mouse.

According to an aspect of the present invention there is provided an isolated peptide being five amino acids which consists of an amino acid sequence represented by the formula $X_1$-$X_2$-$X_3$-$X_4$-$X_5$ (SEQ ID NO: 5), wherein
(i) $X_1$ and $X_3$ are any amino acids;
(ii) $X_2$ is proline or an analogue or derivative thereof;
(iii) $X_4$ is not proline;
(iv) the peptide is capable of reducing the amount of dexamethasone-induced spleen and/or thymus weight loss in a mouse.

According to an aspect of the present invention there is provided an isolated peptide being seven amino acids which consists of an amino acid sequence represented by the formula $X_1$-$X_2$-$X_3$-$X_4$-$X_5$-$X_6$-$X_7$ (SEQ ID NO: 6), wherein
(i) $X_1$, $X_5$ and $X_6$ are any amino acids;
(ii) $X_2$, $X_3$ and $X_7$ is proline or an analogue or derivative thereof;
(iii) $X_4$ is not proline; and
(iv) the peptide is capable of reducing the amount of dexamethasone-induced spleen and/or thymus weight loss in a mouse.

According to an aspect of the present invention there is provided a pharmaceutical composition comprising the peptide disclosed herein as an active agent and a physiologically acceptable carrier.

According to embodiments of the present invention, the derivative of proline is selected from the group consisting of N-methyl proline, alpha-methyl proline and α-aminobutyric acid.

According to embodiments of the present invention, the peptide is 6 amino acids long.

According to embodiments of the present invention, the peptide comprises an amino acid which is attached to the N terminus of $X_1$, the amino acid being selected from the group consisting of alanine, valine, leucine, cysteine, isoleucine, methionine and a derivative or analogue thereof.

According to embodiments of the present invention, the amino acid which is attached to the N terminus of $X_1$ is leucine or a derivative or analogue thereof.

According to embodiments of the present invention, the amino acid which is attached to the N terminus of $X_1$ is a D-amino acid.

According to embodiments of the present invention, the peptide is 7 amino acids long.

According to embodiments of the present invention, the $X_4$ is alanine or an analogue or derivative thereof.

According to embodiments of the present invention, the $X_5$ is selected from the group consisting of tyrosine, phenylalanine, tryptophan and a derivative or analogue thereof.

According to embodiments of the present invention, the $X_5$ is tyrosine.

According to embodiments of the present invention, the isolated peptide comprises an amino acid sequence as set forth in SEQ ID NO: 4.

According to embodiments of the present invention, the isolated peptide consists of an amino acid sequence as set forth in SEQ ID NO: 4.

According to embodiments of the present invention, the peptide comprises the amino acid sequence as set forth in SEQ ID NO: 18.

According to embodiments of the present invention, the peptide consists of the amino acid sequence as set forth in SEQ ID NO: 18.

According to embodiments of the present invention, the isolated peptide is 5 amino acids.

According to embodiments of the present invention, the $X_4$ is selected from the group consisting of alanine, proline, a derivative or analogue of alanine and a derivative or analogue of proline.

According to embodiments of the present invention, the derivative or analogue of proline is selected from the group consisting of N-methyl proline, alpha-methyl proline and α-aminobutyric acid.

According to embodiments of the present invention, the amino acid sequence comprises the sequence as set forth in SEQ ID NO: 3.

According to embodiments of the present invention, the isolated peptide consists of the amino acid sequence as set forth in SEQ ID NO: 3, SEQ ID NO: 7 or SEQ ID NO: 18.

According to embodiments of the present invention, the $X_3$ is leucine.

According to embodiments of the present invention, the $X_1$ and/or $X_3$ are D amino acids.

According to embodiments of the present invention, the peptide is a stapled peptide.

According to embodiments of the present invention, the peptide is a cyclic peptide.

According to embodiments of the present invention, the order of the sequence is reversed and all of the amino acids are of the D-type.

According to embodiments of the present invention, the peptide is attached to a cell penetrating moiety.

According to embodiments of the present invention, the cell penetrating moiety is attached to an N-terminus of the peptide.

According to embodiments of the present invention, the peptide is for use in treating the inflammatory or degenerative disease.

According to embodiments of the present invention, the disease associated with apoptosis is an inflammatory or degenerative disease.

According to embodiments of the present invention, the inflammatory disease is an autoimmune disease.

According to embodiments of the present invention, the degenerative disease is a neurodegenerative disease.

According to embodiments of the present invention, the disease associated with apoptosis is selected from the group consisting of age-related macular degeneration (AMD), retinitis pigmentosa, stroke and myocardial infarction.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Peptides used in the screen were as follows:

| | |
|---|---|
| PPLPY | SEQ ID NO: 3 |
| LPPLAYP | SEQ ID NO: 4 |
| PLPYP | SEQ ID NO: 9 |
| PPL | SEQ ID NO: 10 |
| PLP | SEQ ID NO: 11 |
| PYP | SEQ ID NO: 12 |
| LPGLPYP | SEQ ID NO: 13 |
| LPPLGYP | SEQ ID NO: 14 |
| LAPLPYP | SEQ ID NO: 15 |
| LPALPYP | SEQ ID NO: 16 |

Figure 2:
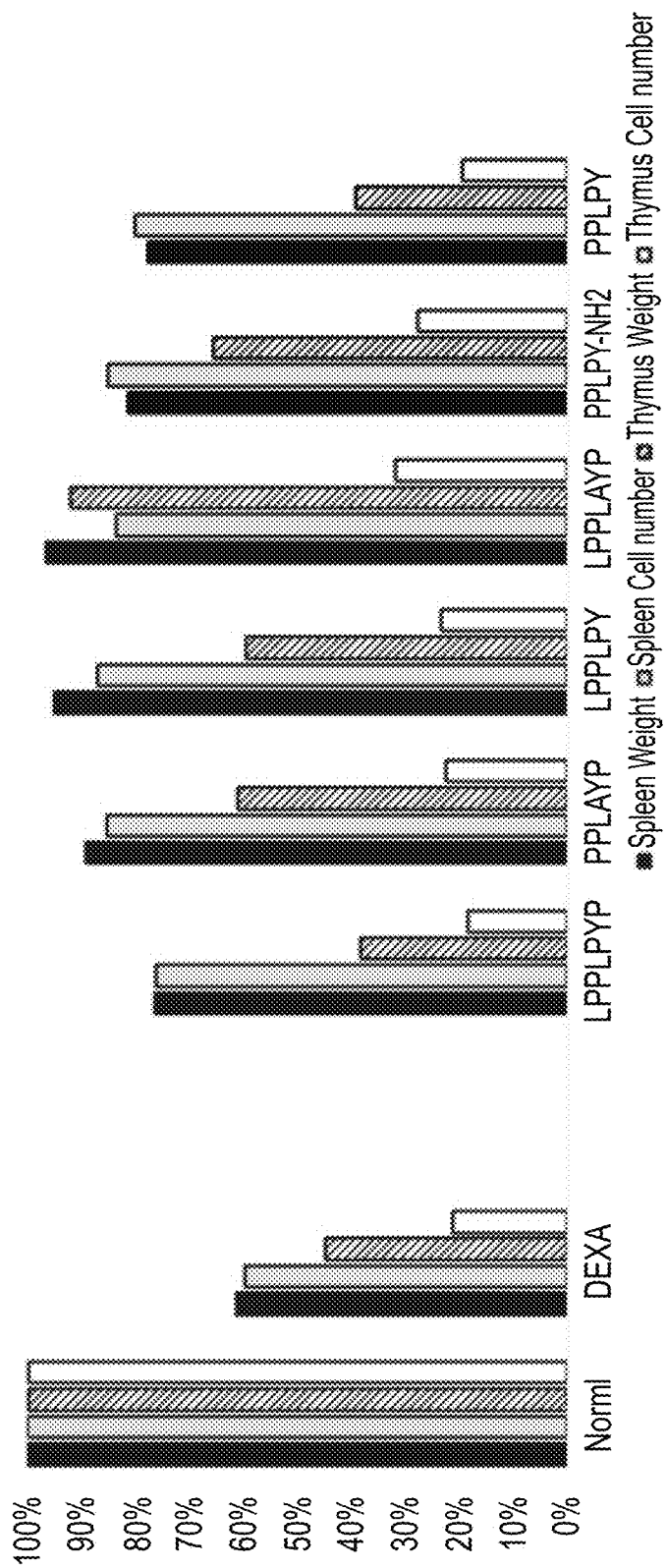

FIG. 2 is a graph illustrating the effect of exemplary peptides on spleen weight, spleen cell number, thymus weight and thymus cell number.

Peptides used in the screen were as follows:

| | |
|---|---|
| LPPLPYP (control) | SEQ ID NO: 2 |
| PPLAYP | SEQ ID NO: 18 |
| LPPLPY | SEQ ID NO: 7 |
| LPPLAYP | SEQ ID NO: 4 |
| PPLPY-NH2 | SEQ ID NO: 19 |
| PPLPY | SEQ ID NO: 3 |

DESCRIPTION OF SPECIFIC EMBODIMENTS OF THE INVENTION

The present invention, in some embodiments thereof, relates to compositions and methods of using same for treating inflammatory and autoimmune diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Peptide bonds are almost exclusively found in a trans conformation with a torsion angle omega close to 180° while only a very limited portion is observed in the cis conformation, with an omega angle of around 0°. The energetic barrier between the trans/cis configurations is approximately 20 [kcal/mol] and the trans isomer is energetically favored by ~2.5 [kcal/mol]. Among the 20 canonical amino acids, proline plays a special role. The proline peptide bond with the preceding amino acid residue (Xaa-Pro, Xaa denoting any amino acid) lacks the amide hydrogen so that this peptide bond cannot act as hydrogen bond donor and the energy barrier as well as the energetic gap is significantly reduced to ~13 and ~0.5 [kcal/mol] respectively [2], shifting the trans/cis equilibrium towards the cis configuration. The large changes in omega angle associated with the proline trans/cis isomerization process (0 to 180) are modulated by both intra and inter-molecular interactions, and have a dramatic influence on the structural activity relation of the polypeptide chain. Thus Proline isomerization is emerging as a critical component in controlling the activity of many biological processes. This is specifically relevant for short peptides in which the cis configuration could occupy more than 30% of the conformational population, depending on the preceding residue.

The multi conformational proline effect, is further known to be manifested in proline residues located as the second residue from the N-terminus of the peptide (penultimate proline). Truncation of the 1$^{st}$ N-terminal residue in peptide containing penultimate proline usually results in peptide conformational change. In a data set of 58 peptides it was found that nearly 80% of the peptides showed this effect [Glover, M. S., et al., 2014 J Am Soc Mass Spectrom. 26(3): p. 444-5].

The multi-proline peptide LPPLPYP (SEQ ID NO: 2), also known as IPL344 and Stressin-1) is a short 7 amino acids peptide that protects cells of various types from pro-apoptotic pressures and activates the Akt signaling system. It is a candidate for treating inflammatory and autoimmune diseases.

Figure 1:
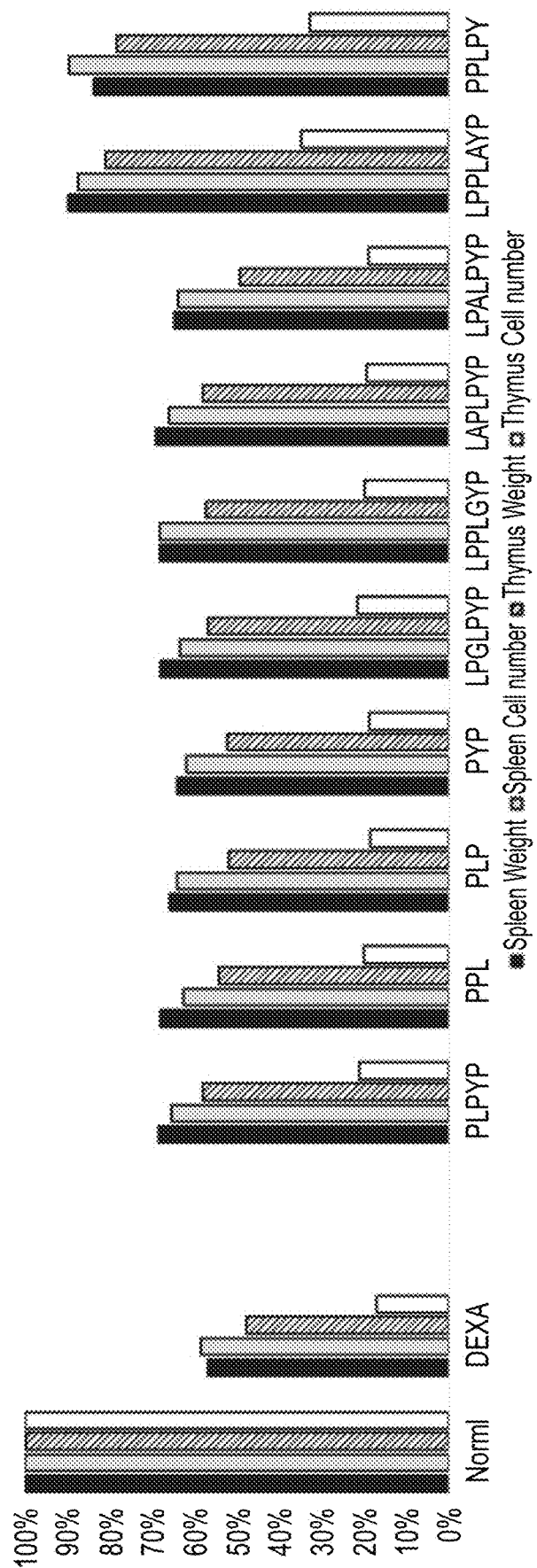
FIG. 1 is a graph illustrating the effect of exemplary peptides on spleen weight, spleen cell number, thymus weight and thymus cell number.

Considering the delicate conformational nature of prolines, the present inventors set out to determine whether the trans proline configuration dominates the functionality of all of the four proline residues of the LPPLPYP (SEQ ID NO: 2) peptide. The present inventors surprisingly found that substituting the penultimate proline for an alanine resulted in a peptide (SEQ ID NO: 4) that significantly reduced the amount of dexamethasone-induced spleen and/or thymus weight loss in a mouse (FIG. 1). In sharp contrast, substituting the penultimate proline for a glycine resulted in a peptide that lacked this activity.

Whilst further reducing the present invention to practice, the present inventors found that removing the first and last amino acid of SEQ ID NO: 2, also resulted in a peptide (having a sequence as set forth in SEQ ID NO: 3) that significantly reduced the amount of dexamethasone-induced spleen and/or thymus weight loss in a mouse.

The present inventors conclude that short peptides based on SEQ ID NOs: 3 and 4 hold promise for the treatment inflammatory and autoimmune diseases.

Whilst further reducing the present invention to practice, the present inventors found that an additional peptide (SEQ ID NO: 18) which conformed to the formula as set forth in SEQ ID NO: 17 showed a significant improvement in reduction of the amount of dexamethasone-induced spleen and/or thymus weight loss in mice (see FIG. 2).

The present inventors further showed that exemplary peptides which fall under either of the disclosed general formulae display a significant improvement compared with the base peptide (SEQ ID NO: 2) for reducing the amount of dexamethasone-induced spleen and/or thymus weight loss in mice.

The term "peptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells.

The present invention also covers derivatives (with modification and/or addition of a chemical function to the amino acid side chain, without a chemical change in the peptidic backbone) and analogues (with modification and/or addition of a chemical function within the peptidic backbone, for example, an N-terminus or C-terminus modification, a peptide bond modification, an amino acid modification not defined as "derivative"), complexes with other species such as a metal ion (e.g. copper, zinc, manganese, magnesium, and others).

Such modifications include, but are not limited to N terminus modification, C terminus modification, polypeptide bond modification, including, but not limited to, CH2-NH, CH2-S, CH2-S=O, O=C—NH$_2$, CH2-O, CH2-CH2, S=C—NH$_2$, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (~C(R)H—C—O—O—C(R)—N—), ketomethylen bonds (—CO—CH2-), α-aza bonds (~NH—N(R)—CO—), wherein R is any alkyl, e.g., methyl, carba bonds (—CH2-NH—), hydroxyethylene bonds (~CH(OH)—CH2-), thioamide bonds (—CS—NH—), olefinic double bonds (~CH=CH—), retro amide bonds (~NH—CO—), polypeptide derivatives (~N(R)—CH2—CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acids such as the analogue Phenylglycine, TIC, naphthylelanine (Nol), ring-methylated derivatives of Phe, halogenated derivatives of Phe or o-methyl-Tyr.

Proline may be replaced for synthetic, non-natural acids such as the derivatives N-methyl proline, alpha-methyl proline and the analogue α-aminobutyric acid.

Other non-natural amino acids are summarized in Table 2, herein below.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |

TABLE 2-continued

| Non-conventional amino acid | Code | Non-conventional amino acid | Code |
|---|---|---|---|
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine 2-aminoadipic acid | pTyr | O-methyl-tyrosine hydroxylysine | |

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acid) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$COOH]—CO— for aspartic acid. Those non-conservative substitutions which fall under the scope of the present invention are those which still constitute a peptide having anti-bacterial properties.

As mentioned, the N and C termini of the peptides of the present invention may be protected by functional groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (~CO—R1) and alkoxy carbonyl or aryloxy carbonyl groups (~CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include $CH_3$-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —$N(ethyl)_2$, —N(methyl) (ethyl), —NH(benzyl), —N(C1-C4 alkyl) (benzyl), —NH(phenyl), —N(C, 1-C4 alkyl) (phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

According to a particular embodiment, the peptide is attached to a cell penetrating moiety.

As used herein, the term "cell penetrating moiety" refers to a moiety (e.g. a lipid, such as palmitic acid) which enhances translocation of an attached peptide across a cell membrane. In a particular embodiment, the cell penetrating moiety is not a peptide moiety. The moiety may be attached to the N or to the C terminus.

The peptides of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The present inventors also conceive of stapled peptides.

The term "stapled peptide" as used herein refers to a peptide having a selected number of standard or non-standard amino acids, and further having at least two moieties capable of undergoing reaction to promote carbon-carbon bond formation, that has been contacted with a reagent to generate at least one cross-linker between the at least two moieties, which modulates, for example, peptide stability.

The term "stapling" as used herein introduces into a peptide at least two moieties capable of undergoing reaction to promote carbon-carbon bond formation that can be contacted with a reagent to generate at least one cross-linker between the at least two moieties. Stapling provides a constraint on a secondary structure, such as an .alpha.-helix structure. The length and geometry of the cross-linker can be optimized to improve the yield of the desired secondary structure content. The constraint provided can, for example, prevent the secondary structure from unfolding and/or can reinforce the shape of the secondary structure. A secondary structure that is prevented from unfolding is, for example, more stable.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the peptides of the present invention can also be synthesized using in vitro expression systems. These methods are well known in the art and the components of the system are commercially available.

The peptides described herein are capable of reducing the amount of dexamethasone-induced spleen and/or thymus weight loss in a mouse—e.g. following injection (IP) with 100 μg of Dexamethasone.

In another embodiment, the peptides described herein are capable of interfering and blocking both TNF-α and IL-6 secretion by macrophage cells in response to innate activators such as lipopolysaccharide (LPS) and CpG oligonucleotides.

Additionally or alternatively, the peptides described herein are capable or reducing, preventing or inhibiting apoptosis in eukaryotic cells. Irrespective of the mechanism by which the peptides of the invention mediates stress responses, and without wishing to be bound by any theory or mechanism of action, it is postulated that the peptides may be capable of binding p53 therefore preventing p53 to be bound to damaged-DNA. The peptide may be tested by analyzing their capacity to inhibit the response to hyperthermia of the L12 cell line (which lacks endogenous p53 activity and had been stably transfected with the p53 gene or a control vector. In these cells, p53 activity induces growth arrest and cell survival rather than apoptosis in response to hyperthermia (as described in WO2012/160563, the contents of which are incorporated herein by reference).

Methods of measuring apoptosis: Apoptosis is an active, gene-directed self-destruction process of the cell and is associated with characteristic morphological and biochemical changes. Nuclear and cytoplasmic condensation and fragmentation of the dying cell into membrane-bound apoptotic bodies are typical characteristics of apoptosis. Another feature of apoptotic cell death is the chromosomal DNA degradation into oligonucleosomal fragments after the activation of specific nucleases.

By "inhibiting apoptosis" or "inhibits apoptotic activity" is meant any decrease in the number of cells that undergo apoptosis relative to an untreated control (i.e. cells not exposed to the peptides of the invention). Preferably, the decrease is at least 25%, more preferably the decrease is at least 50%, and most preferably the decrease is at least one-fold.

Flow cytometry offers a wide variety of possibilities to measure apoptosis. Different methods have been established and implemented, some which stain on the cell surface and some which stain intracellularly.

One of the first approaches was, beside the observation that apoptotic cells shrink and have higher intracellular granularity, to stain with DNA specific fluorochromes (e.g. propidium iodide [PI], ethidium bromide [EtBr]). As soon as a lethal hit is being induced, the DNA starts to change its profile. Apoptotic DNA not only consists of fragmented DNA (visualized as shorter bands, so called DNA ladder, in an agarose gel) but is also partially digested into single nucleotides, so that fluorochromes, like PI or EtBr, have less DNA to stain (Nicoletti et al., 1991). This is typically observed by a shift to the left, called sub-G1 peak, on the specific fluorochrome detection channel in the FACScan™ (from Becton Dickinson, USA).

Another method is the terminal deoxynucleotidyl transferase (TdT)-mediated endlabeling of the DNA strand breaks (TUNEL). The TUNEL method detects DNA strand breaks in cells undergoing apoptosis. TdT is an enzyme which catalyzes the addition of deoxyribonucleotide triphosphate to the 3'-OH ends of double or single-stranded DNA. Unlike normal cells, apoptotic cell nuclei incorporate exogenous nucleotides (dUTP)-DIG in the presence of TdT. An anti-DIG antibody fragment with a conjugated fluorochrome enables the visualization of apoptotic cells. An increase of apoptotic cells causes a higher number of DNA fragments and consequently a brighter fluorescence. An advantage of this method is the very high specificity (Gavrieli et al., 1992). A disadvantage of this method is that it is expensive and can only be used for a small set of samples, because it is time intensive. Therefore, it is not applicable for large screening programs.

The loss of cell membrane polarity and the presentation of increased amounts of phosphatidyl serine (PS) on the outside of the cell membrane during the early phase of apoptosis has led to yet a new approach. Annexin V is a calcium-dependent phospholipid binding protein with high affinity for PS. The cell membrane integrity is maintained in the early and intermediate phases of apoptosis. Early and intermediate apoptotic cells show increased binding of Annexin-FITC and are mainly negative for PI-staining. Late apoptotic stages and necrotic cells become double positive, because of PS presentation on the surface and the PI staining of intracellular nucleic acids due to disintegration of the membrane. This method is also costly and labor intensive.

Other methods for measuring apoptosis in vivo and in vitro are disclosed in U.S. Pat. Nos. 6,726,895 and 6,723,567.

Thus, according to a first aspect of the present invention, there is provided isolated peptide being no longer than six amino acids which comprises an amino acid sequence represented by the formula $X_1$-$X_2$-$X_3$-$X_4$-$X_5$ (SEQ ID NO: 1), (i) wherein $X_1$ is proline or an analogue or derivative thereof;
(ii) wherein $X_2$ is proline or an analogue or derivative thereof;
(iii) wherein $X_3$ is selected from the group of alanine, valine, leucine, cysteine, isoleucine, methionine and a derivative or analogue thereof;
(iv) wherein $X_4$ is selected from the group consisting of alanine, valine, serine, proline and a derivative or analogue thereof;
(v) wherein $X_5$ is any amino acid; and
(vi) wherein the peptide is capable of reducing the amount of dexamethasone-induced spleen and/or thymus weight loss in a mouse.

The peptide according to this aspect of the present invention may be five or six amino acids in length.

Preferably, the amino acids are selected such that the peptide bond between $X_1$ and $X_2$ (at least 50% of the time, at least 60% of the time, at least 70% of the time, at least 80% of the time or even 90% of the time) is in the cis configuration—i.e. the equilibrium is shifted towards a cis configuration; and the peptide bond between $X_3$ and $X_4$ (at least 50% of the time, at least 60% of the time, at least 70% of the time, at least 80% of the time or even 90% of the time) is in the trans configuration—i.e. the equilibrium is shifted towards a trans configuration.

Methods of testing the cis \trans configuration of a peptide bond are known in the art and include for example NMR.

In one embodiment, $X_4$ is selected from the group consisting of alanine, proline, a derivative or analogue of alanine and a derivative or analogue of proline.

According to a particular embodiment, the derivative or analogue of proline is N-methyl proline, alpha-methyl proline or α-aminobutyric acid.

In one embodiment, the peptide comprises the sequence as set forth in SEQ ID NO: 3 (PPLPY).

In another embodiment, the peptide consists of the sequence as set forth in SEQ ID NO: 3 (PPLPY).

In another embodiment, the peptide consists of the sequence as set forth in SEQ ID NO: 7 (LPPLPY).

In a particular embodiment, $X_1$ and/or $X_3$ may be D amino acids, such as the peptide as set forth in SEQ ID NO: 20 (d-LPPLPY).

According to another aspect of the present invention, there is provided isolated peptide being no longer than ten amino acids which comprises an amino acid sequence represented by the formula $X_1$-$X_2$-$X_3$-$X_4$-$X_5$-$X_6$ (SEQ ID NO: 17),
 (i) wherein $X_1$ is proline, or an analogue or derivative thereof;
 (ii) wherein $X_2$ is proline, or an analogue or thereof;
 (iii) wherein $X_3$ is selected from the group of alanine, valine, leucine, cysteine, isoleucine, methionine and a derivative or analogue thereof;
 (iv) wherein $X_4$ is selected from the group consisting of alanine, valine, serine and a derivative or analogue thereof;
 (v) wherein $X_5$ is any amino acid;
 (vi) wherein $X_6$ proline or an analogue or derivative thereof; and
 (vii) wherein the peptide is capable of reducing the amount of dexamethasone-induced spleen and/or thymus weight loss in a mouse.

Preferably, the amino acids are selected such that the peptide bond between $X_1$ and $X_2$ (at least 50% of the time, at least 60% of the time, at least 70% of the time, at least 80% of the time or even 90% of the time) is in the cis configuration—i.e. the equilibrium is shifted towards a cis configuration; and the peptide bond between $X_3$ and $X_4$ (at least 50% of the time, at least 60% of the time, at least 70% of the time, at least 80% of the time or even 90% of the time) is in the trans configuration—i.e. the equilibrium is shifted towards a trans configuration; and the peptide bond between $X_5$ and $X_6$ (at least 50% of the time, at least 60% of the time, at least 70% of the time, at least 80% of the time or even 90% of the time) is in the cis configuration—i.e. the equilibrium is shifted towards a cis configuration.

In one embodiment, the peptide of this aspect of the present is 6 amino acids in length.

An example of such a peptide is the one set forth in SEQ ID NO: 18 (PPLAYP).

Preferred non-naturally occurring amino acids which can be used to replace proline include, but are not limited to N-methyl proline, alpha-methyl proline and α-aminobutyric acid.

The present inventors contemplate an additional amino acid attached at the N-terminus of $X_1$ of SEQ ID NO: 17.

The additional amino acid is preferably selected such that the peptide bond between it and $X_1$ (at least 50% of the time, at least 60% of the time, at least 70% of the time, at least 80% of the time or even 90% of the time) is in the cis configuration—i.e. the equilibrium is shifted towards a cis configuration.

Candidate amino acids include, but are not limited to alanine, valine, leucine, cysteine, isoleucine, methionine and a derivative or analogue thereof.

In a particular embodiment the additional amino acid attached to the N terminus of $X_1$ is leucine or a derivative or analogue thereof.

In a further embodiment, the additional amino acid attached to the N terminus of $X_1$ is a D-amino acid.

Thus, the present inventors conceive of peptides having 7 amino acids and comprising the formula as set forth in SEQ ID NO: 17.

According to a particular embodiment, $X_4$ is alanine or analogue or derivative thereof.

According to still another embodiment $X_5$ is selected from the group consisting of tyrosine, phenylalanine, tryptophan and a derivative or analogue thereof.

An example of an amino acid which is contemplated for $X_5$ is tyrosine.

An example of an amino acid which is contemplated for $X_3$ is leucine.

The peptide of this aspect of the present invention may comprise an amino acid sequence as set forth in SEQ ID NO: 4 (LPPLAYP). Such a peptide may be 7, 8, 9 or 10 amino acids.

The peptide of this aspect of the present invention may consist of an amino acid sequence as set forth in SEQ ID NO: 4.

For the peptides of this aspect of the present invention $X_1$ and/or $X_3$ and/or $X_5$ may be D amino acids, such as for example d-LPPLAYP (SEQ ID NO: 21).

For any of the peptides described herein, the present invention also contemplates retro-inverso peptides. Such peptides are resistant to proteases and consist of D-amino acids in reversed order, resulting in an altered peptide backbone but unchanged orientation of the side chains.

According to still another aspect of the present invention there is provided another isolated peptide being five amino acids which consists of an amino acid sequence represented by the formula $X_1$-$X_2$-$X_3$-$X_4$-$X_5$ (SEQ ID NO: 5), wherein
 (i) $X_1$ and $X_3$ are any amino acids;
 (ii) $X_2$ is proline or an analogue or derivative thereof;
 (iii) $X_4$ is not proline;
 (iv) the peptide is capable of reducing the amount of dexamethasone-induced spleen and/or thymus weight loss in a mouse.

Preferably the amino acids are selected such that the peptide bond between $X_1$-$X_2$ (at least 50% of the time, at least 60% of the time, at least 70% of the time, at least 80% of the time or even 90% of the time) is in the cis configuration—i.e. the equilibrium is shifted towards a cis configuration; and the peptide bond between $X_3$-$X_4$ (at least 50% of the time, at least 60% of the time, at least 70% of the time, at least 80% of the time or even 90% of the time) is in the trans configuration—i.e. the equilibrium is shifted towards a trans configuration.

According to still another aspect of the present invention there is provided an isolated peptide being seven amino acids which consists of an amino acid sequence represented by the formula $X_1$-$X_2$-$X_3$-$X_4$-$X_5$-$X_6$-$X_7$ (SEQ ID NO: 6), wherein
(i) $X_1$, $X_5$ and $X_6$ are any amino acids;
(ii) $X_2$, $X_3$ and $X_7$ is proline or an analogue or derivative thereof;
(iii) $X_4$ is not proline; and
(iv) the peptide is capable of reducing the amount of dexamethasone-induced spleen and/or thymus weight loss in a mouse.

Preferably the amino acids are selected such that the peptide bond between $X_1$-$X_2$ (at least 50% of the time, at least 60% of the time, at least 70% of the time, at least 80% of the time or even 90% of the time) is in the cis configuration—i.e. the equilibrium is shifted towards a cis configuration; the peptide bond between $X_2$-$X_3$ (at least 50% of the time, at least 60% of the time, at least 70% of the time, at least 80% of the time or even 90% of the time) is in the cis configuration—i.e. the equilibrium is shifted towards a cis configuration; the peptide bond between $X_6$-$X_7$ (at least 50% of the time, at least 60% of the time, at least 70% of the time, at least 80% of the time or even 90% of the time) is in the cis configuration—i.e. the equilibrium is shifted towards a cis configuration; and the peptide bond between $X_4$-$X_5$ (at least 50% of the time, at least 60% of the time, at least 70% of the time, at least 80% of the time or even 90% of the time) is in the trans configuration—i.e. the equilibrium is shifted towards a trans configuration.

The peptides described herein may be used for treating a myriad of diseases including those associated with stress-associated responses. These include pathological conditions such as neurodegenerative diseases (e.g. stroke, Parkinson's, and Alzheimer's disease), myocardial infarction, exposure to radiation or chemotherapeutic agents, inflammation, injuries (e.g., burns and central nervous system injuries), cell aging, hyperthermia, seizures, hypoxias (e.g., ischemia and stroke), and in transplant tissues and organs prior to transplanting.

These conditions also include autoimmune diseases, characterized by a state of immunization of an individual against at least one of the body's normal constituents. These phenomena are observed in particular in pathologies including, but not limited to infections associated with SLE (Systemic Lupus Erythematosus disease), Gougerot-Sjogren syndrome (or Sjogren's disease) and rheumatoid polyarthritis, as well as pathologies such as sarcoidosis and osteopenia, spondyloarthritis, scleroderma, multiple sclerosis, amyotrophic lateral sclerosis (ALS), hyperthyroidism, Addison's disease, autoimmune hemolytic anemia, Crohn's disease, Goodpasture's syndrome, Graves' disease, Hashimoto's thyroiditis, idiopathic purpura hemorrhage, insulin-dependent diabetes, myasthenia, pemphigus vulgaris, pernicious anemia, post-streptococcal glomerulonephritis, psoriasis and spontaneous sterility, as well as immediate or delayed phenomena observed during graft rejections and graft-versus host disease. In one particular embodiment, the peptides of the invention are useful for the treatment of multiple sclerosis. In another embodiment, the peptides of the invention are useful for the treatment of ischemia or myocardial infarction.

Other diseases contemplated by the present invention include but not limited to, Alzheimer's disease, Parkinson's disease, secondary degeneration after trauma, stroke, CNS intoxication, glaucoma, macular degeneration, type 1 diabetes, multiple sclerosis, systemic lupus erythematosis, autoimmune uveitis, graft versus host disease, graft rejection, arthritis, systemic inflammatory response syndrome (SIRS) inflammatory bowel disease (IBD), adult respiratory distress syndrome (ARDS), psoriasis, atherosclerosis, myocardial infarction, radiation disease, hyperthermia, hypoxia, fulminant toxic liver, kidney failure, infertility and many others.

The phenomenon of graft rejection is a state of immunization of an individual against foreign constituents (bodily fluids such as blood, cerebrospinal fluid, etc., cells, tissues, organs, antibodies, etc.) deliberately implanted into the patient.

As used herein, the terms "degenerative disorder" "degenerative disease" and "degenerative condition" are directed to any disorder, disease or condition characterized by inappropriate cell proliferation or inappropriate cell death or in some cases, both, or aberrant or disregulated apoptosis. These conditions also include conditions in which, although appropriate and regulated at the level of a single cell, excessive apoptosis is associated with organ dysfunction or failure.

In one embodiment, the peptides are useful to prevent cell death in non-malignant tissue or cells in a subject having a neoplastic disorder and undergoing chemotherapy and/or radiation therapy for the treatment of cancer.

The terms "inflammatory disease" and "inflammatory condition", as used herein, mean any disease or condition in which an excessive or unregulated inflammatory response leads to excessive inflammatory symptoms, host tissue damage, or loss of tissue function.

In one embodiment, the inflammatory disease or condition is an autoimmune disease.

In another embodiment, the inflammatory disease or condition has an etiology associated with production of at least one pro-inflammatory cytokine selected from IL-6 and TNF-α.

In another embodiment, the disease or condition is selected from the group consisting of: Alzheimer's disease, Parkinson's disease, secondary degeneration after trauma, stroke, CNS intoxication, glaucoma, macular degeneration, myocardial infarction, radiation disease, hyperthermia, hypoxia, fulminant toxic liver, kidney failure and infertility.

In still another embodiment, the disease includes retinitis pigmentosa and macular degeneration.

In another embodiment, the disease includes stroke or myocardial infarction.

The peptides may be provided per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptides accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

The preparation of pharmaceutical compositions, which contain peptides or polypeptides as active ingredients is well known in the art. Typically, such compositions are prepared as indictable, either as liquid solutions or suspensions, however, solid forms, which can be suspended or solubilized prior to injection, can also be prepared. The preparation can also be emulsified. The active therapeutic ingredient is mixed with inorganic and/or organic carriers, which are pharmaceutically acceptable and compatible with the active ingredient. Carriers are pharmaceutically acceptable excipients (vehicles) comprising more or less inert substances when added to a pharmaceutical composition to confer suitable consistency or form to the composition. Suitable carriers are, for example, water, saline, dextrose, glycerol, ethanol, or the like and combinations thereof. In addition, if desired, the composition can contain minor amounts of auxiliary substances such as wetting or emulsifying agents and pH buffering agents, which enhance the effectiveness of the active ingredient.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al., 1975).

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compounds or active agents in a single composition or may contain a divided pharmacologically, biologically, therapeutically, or chemically effective amount. The total effective amount can then be administered in cumulative units containing, in total, an effective amount of the active agent.

A therapeutically effective amount of a peptide of the invention is an amount that when administered to a patient is capable of exerting an anti-apoptotic activity and/or an anti-inflammatory activity. Assays for detecting the anti-apoptotic activity of the peptide of the invention include, but are not limited to, staining DNA with specific fluorochromes such as propidium iodide and ethidium bromide, Annexin V assays, TUNEL assays and the like; certain non-limitative examples of such assays are presented in the Examples below. Assays for detecting anti-inflammatory activity of the peptides are also well known in the art.

Although an appropriate dosage of a peptide of the invention varies depending on the administration route, age, body weight sex or conditions of the patient, and should be determined by the physician in the end, the dose suitable for adult humans can generally be between about 0.2-2000 mg/kg body weight, preferably between about 2-200 mg/kg.

The pharmaceutical compositions of the present invention comprises one or more compounds of the present invention, and one or more excipients or diluents. In one embodiment, one or more of the compounds, or solvates, or salts of these compounds.

The term "pharmaceutically acceptable salt" as used herein, refers to salts which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

The pharmaceutical compositions can be administered locally or systemically by any conventional and appropriate route including, but not limited to, oral, intraperitoneal, parenteral, intravenous, intramuscular, subcutaneous, transdermal, intrathecal, topical, rectal, buccal, inhalational or intranasal.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, like suspending agents, such as sorbitol syrup, methyl cellulose, glucose/sugar syrup, gelatin, hydroxyethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

For administration by inhalation, the peptides for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

The pharmaceutical compositions of the invention are also useful for topical and intralesional application. As used herein, the term "topical" means "pertaining to a particular surface area", e.g. skin and mucosa, and the topical agent applied to a certain area of the surface will affect only the area to which it is applied. The formulations of the peptides/peptide analogs may be administered topically as a gel, ointment, cream, emulsion, sustained release formulation including a transdermal patch, and may comprise liposomes and any other pharmaceutically acceptable carrier suitable for administration of the drug topically. The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Dexamethasone is a corticosteroid medication that induces apoptosis of immune cells and lymphomyeloid tissues. BALB/c mice were used to examine the ability of candidate peptides to rescue lymphocyte cells from apoptosis. Mice were injected IP with 100 μg of Dexamethasone. Dexamethasone-treated mice received immediately following and 24-hours after dexamethasone treatment IV injection of candidate peptides (250 or 400 μg peptide/mouse). Mice were sacrificed 48 hours after the first treatment. The spleen and the thymus were weighted and full cell count of both organs was performed.

Peptides used in the screen were as follows:

```
                           SEQ ID NO: 3
PPLPY

SEQ ID NO: 4
LPPLAYP

SEQ ID NO: 9
PLPYP

SEQ ID NO: 10
PPL

SEQ ID NO: 11
PLP

SEQ ID NO: 12
PYP
```

-continued
```
                           SEQ ID NO: 13
LPGLPYP

SEQ ID NO: 14
LPPLGYP

SEQ ID NO: 15
LAPLPYP

SEQ ID NO: 16
LPALPYP
```

Results:

Dexamethasone induced spleen and thymus weight loss and reduction in spleen cell count of about 50%. Thymus cell count was reduced by almost 80% compared to normal mice. Two of the peptides had significant effect in reduction of spleen and thymus weight loss as well as reduction of cell count loss—SEQ ID NO: 3 and SEQ ID NO: 4 (see FIG. 1). There was no difference between the 2 treatment doses (250 or 400 μg/mouse).

Example 2

BALB/c mice were used to examine the ability of candidate peptides to rescue lymphocyte cells from apoptosis. Mice were injected IP with 100 μg of Dexamethasone. Dexamethasone-treated mice received immediately following and 24-hours after dexamethasone treatment IV injection of candidate peptides (200 μg peptide/mouse). Mice were sacrificed 48 hours after the first treatment. The spleen and the thymus were weighted and full cell count of both organs was performed.

Peptides used in the screen were as follows:

```
                              SEQ ID NO: 2
LPPLPYP   (control)

SEQ ID NO: 18
PPLAYP

SEQ ID NO: 7
LPPLPY

SEQ ID NO: 4
LPPLAYP

SEQ ID NO: 3
PPLPY

SEQ ID NO: 19
PPLPY-NH₂
```

Results

The results are provided in FIG. 2. Each of the tested peptides showed an improvement over the control peptide (SEQ ID NO: 2).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, the priority document of this application is hereby incorporated herein by reference in its entirety.

What is claimed is:

1. An isolated peptide consisting of the amino acid sequence as set forth in SEQ ID NO: 21, wherein the amino acid at position 1 is a D-amino acid, wherein the peptide is capable of reducing the amount of dexamethasone-induced spleen and/or thymus weight loss in a mouse.

2. A pharmaceutical composition comprising the isolated peptide of claim 1.

* * * * *

SEQUENCE LISTING

```
<160> NUMBER OF SEQ ID NOS: 21

<210> SEQ ID NO 1
<211> LENGTH: 5
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(2)
<223> OTHER INFORMATION: X  is proline or an analogue or derivative
      thereof
<220> FEATURE:
<221> NAME/KEY: MISC_FEATURE
<222> LOCATION: (3)..(3)
<223> OTHER INFORMATION: X  is  alanine, valine, leucine, cysteine,
      isoleucine, methionine or a derivative or analogue thereof
<220> FEATURE:
<221> NAME/KEY: MISC_FEATURE
<222> LOCATION: (4)..(4)
<223> OTHER INFORMATION: X  is   alanine, valine, serine, proline or a
      derivative or analogue thereof
<220> FEATURE:
<221> NAME/KEY: MISC_FEATURE
<222> LOCATION: (5)..(5)
<223> OTHER INFORMATION: X  is  any amino acid

<400> SEQUENCE: 1

Xaa Xaa Xaa Xaa Xaa
1               5

<210> SEQ ID NO 2
<211> LENGTH: 7
<212> TYPE: PRT
<213> ORGANISM: Artificial sequence
<220> FEATURE:
<223> OTHER INFORMATION: Stressin-1 amino acid sequence

<400> SEQUENCE: 2

Leu Pro Pro Leu Pro Tyr Pro
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic Peptide

<400> SEQUENCE: 3

Pro Pro Leu Pro Tyr
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic Peptide

<400> SEQUENCE: 4
```

```
Leu Pro Pro Leu Ala Tyr Pro
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: X2 is proline or an analogue or derivative
      thereof
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X  is not proline
<220> FEATURE:
<221> NAME/KEY: misc_feature
<222> LOCATION: (5)..(5)
<223> OTHER INFORMATION: Xaa can be any naturally occurring amino acid

<400> SEQUENCE: 5

Xaa Xaa Xaa Xaa Xaa
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(3)
<223> OTHER INFORMATION: X is proline or an analogue or derivative
      thereof
<220> FEATURE:
<221> NAME/KEY: MISC_FEATURE
<222> LOCATION: (4)..(4)
<223> OTHER INFORMATION: X is not proline
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: X is proline or an analogue or derivative
      thereof

<400> SEQUENCE: 6

Xaa Xaa Xaa Xaa Xaa Xaa Xaa
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic Peptide
```

<400> SEQUENCE: 7

Leu Pro Pro Leu Pro Tyr
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic Peptide

<400> SEQUENCE: 8

Pro Pro Leu Pro Tyr Pro
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic Peptide

<400> SEQUENCE: 9

Pro Leu Pro Tyr Pro
1               5

<210> SEQ ID NO 10
<211> LENGTH: 3
<212> TYPE: PRT
<213> ORGANISM: Artificial sequence
<220> FEATURE:
<223> OTHER INFORMATION: Synthetic Peptide

<400> SEQUENCE: 10

Pro Pro Leu
1

<210> SEQ ID NO 11
<211> LENGTH: 3
<212> TYPE: PRT
<213> ORGANISM: Artificial sequence
<220> FEATURE:
<223> OTHER INFORMATION: Synthetic Peptide

<400> SEQUENCE: 11

Pro Leu Pro
1

<210> SEQ ID NO 12
<211> LENGTH: 3
<212> TYPE: PRT
<213> ORGANISM: Artificial sequence
<220> FEATURE:
<223> OTHER INFORMATION: Synthetic Peptide

<400> SEQUENCE: 12

Pro Tyr Pro
1

<210> SEQ ID NO 13
<211> LENGTH: 7
<212> TYPE: PRT
<213> ORGANISM: Artificial sequence
<220> FEATURE:
<223> OTHER INFORMATION: Synthetic Peptide

```
<400> SEQUENCE: 13

Leu Pro Gly Leu Pro Tyr Pro
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic Peptide

<400> SEQUENCE: 14

Leu Pro Pro Leu Gly Tyr Pro
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic Peptide

<400> SEQUENCE: 15

Leu Ala Pro Leu Pro Tyr Pro
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic Peptide

<400> SEQUENCE: 16

Leu Pro Ala Leu Pro Tyr Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X  is proline, or an analogue or derivative
      thereof
<220> FEATURE:
<221> NAME/KEY: MISC_FEATURE
<222> LOCATION: (2)..(2)
<223> OTHER INFORMATION: X  is  proline, or an analogue or thereof
<220> FEATURE:
<221> NAME/KEY: MISC_FEATURE
<222> LOCATION: (3)..(3)
<223> OTHER INFORMATION: X  is  eitherf alanine, valine, leucine,
      cysteine, isoleucine, methionine and a derivative or analogue
      thereof
<220> FEATURE:
<221> NAME/KEY: MISC_FEATURE
<222> LOCATION: (4)..(4)
<223> OTHER INFORMATION: X  is  eitherf alanine, valine, serine and a
      derivative or analogue thereof
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: X  is  proline or an analogue or derivative
```

```
                     thereof

<400> SEQUENCE: 17

Xaa Xaa Xaa Xaa Xaa Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 18

Pro Pro Leu Ala Tyr Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 19

Pro Pro Leu Pro Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D amino acid

<400> SEQUENCE: 20

Leu Pro Pro Leu Pro Tyr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: may be D amino acid
<220> FEATURE:
<221> NAME/KEY: MISC_FEATURE
<222> LOCATION: (3)..(3)
<223> OTHER INFORMATION: may be D amino acid
<220> FEATURE:
<221> NAME/KEY: MISC_FEATURE
<222> LOCATION: (5)..(5)
<223> OTHER INFORMATION: may be D amino acid

<400> SEQUENCE: 21

Leu Pro Pro Leu Ala Tyr Pro
1               5
```